(12) United States Patent
Mugford et al.

(10) Patent No.: US 11,535,875 B2
(45) Date of Patent: Dec. 27, 2022

(54) PARTIAL ENZYMATIC HYDROLYSIS OF TRIACYLGLYCEROLS TO PRODUCE LONG-CHAIN POLYUNSATURATED FATTY ACID

(71) Applicant: DSM IP Assets B.V., Heerlen (NL)

(72) Inventors: Paul Mugford, Halifax (CA); Monika Mueller, Aachen (DE); Martin Schurmann, Juelich (DE)

(73) Assignee: DSM IP ASSETS B.V., Heerlen (NL)

( * ) Notice: Subject to any disclaimer, the term of this patent is extended or adjusted under 35 U.S.C. 154(b) by 923 days.

(21) Appl. No.: 16/066,587

(22) PCT Filed: Dec. 29, 2016

(86) PCT No.: PCT/IB2016/058086
§ 371 (c)(1),
(2) Date: Jun. 27, 2018

(87) PCT Pub. No.: WO2017/115322
PCT Pub. Date: Jul. 6, 2017

(65) Prior Publication Data
US 2021/0207181 A1    Jul. 8, 2021

Related U.S. Application Data

(60) Provisional application No. 62/272,829, filed on Dec. 30, 2015.

(51) Int. Cl.
*C12P 7/6472* (2022.01)
*C12N 9/20* (2006.01)

(52) U.S. Cl.
CPC .............. *C12P 7/6472* (2013.01); *C12N 9/20* (2013.01)

(58) Field of Classification Search
None
See application file for complete search history.

(56) References Cited

U.S. PATENT DOCUMENTS 10,829,748 B2 * 11/2020 De Jong ................ C12N 15/63

FOREIGN PATENT DOCUMENTS

| CN | 1366056 A | 8/2002 |
|---|---|---|
| CN | 104726477 A | 6/2015 |
| EP | 0635574 A1 | 1/1995 |
| EP | 1130100 A1 | 9/2001 |
| WO | WO1993003159 | 2/1993 |
| WO | WO1998046772 | 10/1998 |
| WO | WO1999060102 | 11/1999 |
| WO | WO00/37671 | 6/2000 |
| WO | WO2013043641 A1 | 3/2013 |
| WO | WO2015087833 A1 | 6/2015 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Accession P20261. Feb. 1, 1991 (Year: 1991).*
Accession P32947. Oct. 1, 1993 (Year: 1993).*
Accession P79066. Feb. 16, 2004 (Year: 2004).*
Alexopoulos, C.J., Introductory Mycology, Introductory Mycology, 1952, 482.
Altschul et al., Basic Local Alignment Search Tool, J. Mol. Biol., 1990, 403-410, 215.
Altschul et al., Gapped BLAST and PSI-BLAST: a new generation of protein database search programs, Nucleic Acids Research, 1997, 3389-3402, 25(17).
Arai et al., Cloning and Sequencing of the cDNA encoding lipase I from Trichosporon fermentans WU-C12, FEMS Microbiology Letters, 1997, 183-188, 152.
Ausubel et al, Current Protocols in Molecular Biology Current Protocols in Molecular Biology, Molecular Biiology, Dec. 4, 2003, whole book, Book, John Wiley & Sons, Inc.
Carillo et al., The Multiple Sequence Alignment Problem in Biology, SIAM J. Appl. Math, 1988, 1073-1082, 48(5).
Chang et al., Codon Optimization of Candida rugosa lip 1 Gene for Improving Expression in Pichia pastoris and Biochemical Characterization of the Purified Recombinant LIP1 Lipase, Journal of Agricultural and Food Chemistry, 2006, 815-822, 54(3).
Chang et al., Efficient Production of Active Recombinant Candida rugosa LIP3 Lipase in Pchia pastoris and Biochemical Characterization of the Purified Enzyme, Journal of Agricultural and Food Chemistry, 2006, 5831-5838, 54.
Devereux et al, A comprehensive set of sequence analysis programs for the VAX, Nucleic Acids Research, 1984, 387-395, 12(1).
Fleer et al., Stable Multicopy Vectors for High-Level Secretion of Recombinant Human Serum Albumin by Kluyveromyces Yeasts, Biotechnology, 1991, 968-975, 9, Nature Publishing Group.
Henikoff et al, Amino acid substitution matrices from protein blocks, Biochemistry, 1992, 10915-10919, 89.
J. Sambrook, Molcular Cloning, A Laboratory Manual, 1989, Table of contents, Second.
Needleman et al., A General Method Applicable to the Search for Similarities in the Amino Acid Sequence of Two Proteins, J. Mol. Biol., 1970, 443-453, 48.
Pan et al., Efficient Display of Active *Geotrichum* sp. Lipase on Pichia pastoris Cell Wall and Its Application as a Whole-Cell Biocatalyst to Enrich EPA and DHA in Fish Oil, Journal of Agricultural and Food Chemistry, 2012, 9673-9679, 60.
Russell, Paul R., Transcription of the triose-phosphate-isomerase gene of Schizosaccharomyces pombe initiates from a start point different from that in *Saccharomyces cerevisiae*, Gene, 1985, 125-130, 40.
Shimada et al, cDNA Cloning and Characterization of Geotrichum candidum Lipase II, J. Biochem., 1990, 703-707, 107.

* cited by examiner

*Primary Examiner* — Christian L Fronda
(74) *Attorney, Agent, or Firm* — McBee Moore & Vanik IP, LLC; Susan McBee; Chester Moore

(57) ABSTRACT

Disclosed herein are host cells expressing a polypeptide, wherein the polypeptide hydrolyzes an ester linkage of a triacylglycerol in an oil comprising at least one long-chain polyunsaturated fatty acid, methods for using such host cells, and processes for production of a lipase using such host cells.

9 Claims, No Drawings

Specification includes a Sequence Listing.

SEQUENCE LISTING

<160> NUMBER OF SEQ ID NOS: 3

<210> SEQ ID NO 1
<211> LENGTH: 534
<212> TYPE: PRT
<213> ORGANISM: Candida rugosa

<400> SEQUENCE: 1

```
Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Phe Glu Val Gly
            115                 120                 125

Gly Thr Ser Thr Phe Pro Pro Ala Gln Met Ile Thr Lys Ser Ile Ala
        130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190
```

```
Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
        210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
                260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
        290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
                340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
        370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415

Leu Ala Arg Arg Tyr Phe Leu Asn His Tyr Thr Gly Gly Thr Lys Tyr
                420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
        450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
                500                 505                 510

Gly Lys Asp Asn Phe Arg Thr Ala Gly Tyr Asp Ala Leu Phe Ser Asn
        515                 520                 525

Pro Pro Ser Phe Phe Val
    530

<210> SEQ ID NO 2
<211> LENGTH: 534
<212> TYPE: PRT
<213> ORGANISM: Candida rugosa

<400> SEQUENCE: 2

Ala Pro Thr Ala Lys Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
```

```
                20                  25                  30
Val Gly Asn Leu Arg Phe Lys Asp Pro Val Pro Tyr Ser Gly Ser Leu
             35                  40                  45

Asn Gly Gln Lys Phe Thr Ser Tyr Gly Pro Ser Cys Met Gln Gln Asn
 50                  55                  60

Pro Glu Gly Thr Phe Glu Glu Asn Leu Gly Lys Thr Ala Leu Asp Leu
 65                  70                  75                  80

Val Met Gln Ser Lys Val Phe Gln Ala Val Leu Pro Gln Ser Glu Asp
                 85                  90                  95

Cys Leu Thr Ile Asn Val Val Arg Pro Pro Gly Thr Lys Ala Gly Ala
                100                 105                 110

Asn Leu Pro Val Met Leu Trp Ile Phe Gly Gly Gly Phe Glu Ile Gly
                115                 120                 125

Ser Pro Thr Ile Phe Pro Pro Ala Gln Met Val Thr Lys Ser Val Leu
                130                 135                 140

Met Gly Lys Pro Ile Ile His Val Ala Val Asn Tyr Arg Val Ala Ser
145                 150                 155                 160

Trp Gly Phe Leu Ala Gly Asp Asp Ile Lys Ala Glu Gly Ser Gly Asn
                165                 170                 175

Ala Gly Leu Lys Asp Gln Arg Leu Gly Met Gln Trp Val Ala Asp Asn
                180                 185                 190

Ile Ala Gly Phe Gly Gly Asp Pro Ser Lys Val Thr Ile Phe Gly Glu
                195                 200                 205

Ser Ala Gly Ser Met Ser Val Leu Cys His Leu Ile Trp Asn Asp Gly
                210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Pro Val Asp Gly Thr Tyr Gly Asn
                245                 250                 255

Glu Ile Tyr Asp Leu Phe Val Ser Ser Ala Gly Cys Gly Ser Ala Ser
                260                 265                 270

Asp Lys Leu Ala Cys Leu Arg Ser Ala Ser Ser Asp Thr Leu Leu Asp
                275                 280                 285

Ala Thr Asn Asn Thr Pro Gly Phe Leu Ala Tyr Ser Ser Leu Arg Leu
                290                 295                 300

Ser Tyr Leu Pro Arg Pro Asp Gly Lys Asn Ile Thr Asp Asp Met Tyr
305                 310                 315                 320

Lys Leu Val Arg Asp Gly Lys Tyr Ala Ser Val Pro Val Ile Ile Gly
                325                 330                 335

Asp Gln Asn Asp Glu Gly Thr Ile Phe Gly Leu Ser Ser Leu Asn Val
                340                 345                 350

Thr Thr Asn Ala Gln Ala Arg Ala Tyr Phe Lys Gln Ser Phe Ile His
                355                 360                 365

Ala Ser Asp Ala Glu Ile Asp Thr Leu Met Ala Ala Tyr Pro Gln Asp
                370                 375                 380

Ile Thr Gln Gly Ser Pro Phe Asp Thr Gly Ile Phe Asn Ala Ile Thr
385                 390                 395                 400

Pro Gln Phe Lys Arg Ile Ser Ala Val Leu Gly Asp Leu Ala Phe Ile
                405                 410                 415

His Ala Arg Arg Tyr Phe Leu Asn His Phe Gln Gly Gly Thr Lys Tyr
                420                 425                 430

Ser Phe Leu Ser Lys Gln Leu Ser Gly Leu Pro Ile Met Gly Thr Phe
                435                 440                 445
```

His Ala Asn Asp Ile Val Trp Gln Asp Tyr Leu Leu Gly Ser Gly Ser
        450                 455                 460

Val Ile Tyr Asn Asn Ala Phe Ile Ala Phe Ala Thr Asp Leu Asp Pro
465                 470                 475                 480

Asn Thr Ala Gly Leu Leu Val Asn Trp Pro Lys Tyr Thr Ser Ser Ser
                485                 490                 495

Gln Ser Gly Asn Asn Leu Met Met Ile Asn Ala Leu Gly Leu Tyr Thr
                500                 505                 510

Gly Lys Asp Asn Phe Arg Thr Ala Gly Tyr Asp Ala Leu Met Thr Asn
            515                 520                 525

Pro Ser Ser Phe Phe Val
        530

<210> SEQ ID NO 3
<211> LENGTH: 544
<212> TYPE: PRT
<213> ORGANISM: Geotrichum Candida

<400> SEQUENCE: 3

Gln Ala Pro Thr Ala Val Leu Asn Gly Asn Glu Val Ile Ser Gly Val
1               5                   10                  15

Leu Glu Gly Lys Val Asp Thr Phe Lys Gly Ile Pro Phe Ala Asp Pro
            20                  25                  30

Pro Leu Asn Asp Leu Arg Phe Lys His Pro Gln Pro Phe Thr Gly Ser
        35                  40                  45

Tyr Gln Gly Leu Lys Ala Asn Asp Phe Ser Pro Ala Cys Met Gln Leu
    50                  55                  60

Asp Pro Gly Asn Ser Leu Thr Leu Leu Asp Lys Ala Leu Gly Leu Ala
65                  70                  75                  80

Lys Val Ile Pro Glu Glu Phe Arg Gly Pro Leu Tyr Asp Met Ala Lys
                85                  90                  95

Gly Thr Val Ser Met Asn Glu Asp Cys Leu Tyr Leu Asn Val Phe Arg
            100                 105                 110

Pro Ala Gly Thr Lys Pro Asp Ala Lys Leu Pro Val Met Val Trp Ile
        115                 120                 125

Tyr Gly Gly Ala Phe Val Tyr Gly Ser Ser Ala Ala Tyr Pro Gly Asn
    130                 135                 140

Ser Tyr Val Lys Glu Ser Ile Asn Met Gly Gln Pro Val Val Phe Val
145                 150                 155                 160

Ser Ile Asn Tyr Arg Thr Gly Pro Phe Gly Phe Leu Gly Gly Asp Ala
                165                 170                 175

Ile Thr Ala Glu Gly Asn Thr Asn Ala Gly Leu His Asp Gln Arg Lys
            180                 185                 190

Gly Leu Glu Trp Val Ser Asp Asn Ile Ala Asn Phe Gly Gly Asp Pro
        195                 200                 205

Asp Lys Val Met Ile Phe Gly Glu Ser Ala Gly Ala Met Ser Val Ala
    210                 215                 220

His Gln Leu Ile Ala Tyr Gly Gly Asp Asn Thr Tyr Asn Gly Lys Lys
225                 230                 235                 240

Leu Phe His Ser Ala Ile Leu Gln Ser Gly Gly Pro Leu Pro Tyr His
                245                 250                 255

Asp Ser Ser Ser Val Gly Pro Asp Ile Ser Tyr Asn Arg Phe Ala Gln
            260                 265                 270

Tyr Ala Gly Cys Asp Thr Ser Ala Ser Ala Asn Asp Thr Leu Glu Cys

-continued

```
                275                 280                 285
Leu Arg Ser Lys Ser Ser Ser Val Leu His Asp Ala Gln Asn Ser Tyr
    290                 295                 300
Asp Leu Lys Asp Leu Phe Gly Leu Leu Pro Gln Phe Leu Gly Phe Gly
305                 310                 315                 320
Pro Arg Pro Asp Gly Asn Ile Ile Pro Asp Ala Ala Tyr Glu Leu Phe
                325                 330                 335
Arg Ser Gly Arg Tyr Ala Lys Val Pro Tyr Ile Ser Gly Asn Gln Glu
            340                 345                 350
Asp Glu Gly Thr Ala Phe Ala Pro Val Ala Leu Asn Ala Thr Thr Thr
        355                 360                 365
Pro His Val Lys Lys Trp Leu Gln Tyr Ile Phe Tyr Asp Ala Ser Glu
    370                 375                 380
Ala Ser Ile Asp Arg Val Leu Ser Leu Tyr Pro Gln Thr Leu Ser Val
385                 390                 395                 400
Gly Ser Pro Phe Arg Thr Gly Ile Leu Asn Ala Leu Thr Pro Gln Phe
                405                 410                 415
Lys Arg Val Ala Ala Ile Leu Ser Asp Met Leu Phe Gln Ser Pro Arg
            420                 425                 430
Arg Val Met Leu Ser Ala Thr Lys Asp Val Asn Arg Trp Thr Tyr Leu
        435                 440                 445
Ser Thr His Leu His Asn Leu Val Pro Phe Leu Gly Thr Phe His Gly
    450                 455                 460
Asn Glu Leu Ile Phe Gln Phe Asn Val Asn Ile Gly Pro Ala Asn Ser
465                 470                 475                 480
Tyr Leu Arg Tyr Phe Ile Ser Phe Ala Asn His His Asp Pro Asn Val
                485                 490                 495
Gly Thr Asn Leu Leu Gln Trp Asp Gln Tyr Thr Asp Glu Gly Lys Glu
            500                 505                 510
Met Leu Glu Ile His Met Thr Asp Asn Val Met Arg Thr Asp Asp Tyr
        515                 520                 525
Arg Ile Glu Gly Ile Ser Asn Phe Glu Thr Asp Val Asn Leu Tyr Gly
    530                 535                 540
```

PARTIAL ENZYMATIC HYDROLYSIS OF TRIACYLGLYCEROLS TO PRODUCE LONG-CHAIN POLYUNSATURATED FATTY ACID

CROSS-REFERENCE TO RELATED APPLICATIONS

This application is a National Stage of International Application No. PCT/IB2016/058086 filed Dec. 29, 2016, and which claims the benefit of the filing date of United States Provisional Patent Application No. 62/272,829 filed Dec. 30, 2015, 2014, the entire contents of each of which are hereby incorporated herein by reference in their entireties.

FIELD OF THE INVENTION

The present invention relates to host cells expressing a polypeptide wherein the polypeptide is expressed in the host cell to confer the ability of hydrolyzing an ester linkage of a triacylglycerol in an oil comprising at least one long-chain polyunsaturated fatty acid and methods of using a host cell expressing a polypeptide wherein the polypeptide is expressed in the host cell to confer the ability of hydrolyzing an ester linkage of a triacylglycerol in an oil comprising at least one long-chain polyunsaturated fatty acid. The host cell is used to manufacture sufficient quantities of this polypeptide so as to be useful for commercial manufacture of oil compositions that are enriched in long-chain polyunsaturated fatty acids.

BACKGROUND

Long-chain polyunsaturated fatty acids (LC-PUFAs) such as the omega-3 fatty acids are vital to everyday life and function. For example, the beneficial effects of omega-3 fatty acids like cis-5,8,11,14,17-eicosapentaenoic acid (EPA) and cis-4,7,10,13,16,19-docosahexaenoic acid (DHA) on lowering serum triglycerides are now well established. These compounds are also known for other cardioprotective benefits. Indeed, the American Heart Association has also reported that omega-3 fatty acids can reduce cardiovascular and heart disease risk. Other benefits of LC-PUFAs are those related to the prevention and/or treatment of inflammation, neurodegenerative diseases, and cognitive development. Diets rich in LC-PUFAs like omega-3 fatty acids have also been shown to have beneficial effects for heart disease, cancer, arthritis, allergies, and other chronic diseases.

LC-PUFAs, such as, for example, omega-3 fatty acids, are often derived from marine oils, microbial, and/or algal oils. Such sources typically contain LC-PUFAs in a triacylglycerol form where other undesired fatty acids (e.g., saturated fatty acids) are present alongside a desired LC-PUFA(s) in the triacylglycerol molecule. Thus, purifying and concentrating LC-PUFAs in oils is generally desired.

Various methods of producing LC-PUFA concentrates from oils, such as marine, microbial, and/or algal oils, are known. For example, lipases have been used to transesterify saturated fatty acids from triacylglycerols into ethyl esters. The saturated fatty acids are then removed from the mixture by distillation, and the unsaturated esters are sometimes transesterified back to triacylglycerols. Other methods selectively hydrolyze saturated fatty acids from triacylglycerols with lipases and the resulting free saturated fatty acids are removed by forming a complex with urea. The amount of LC-PUFAs contained in oils obtained by these methods is generally 60 wt. % or higher, or 70 wt. % or higher relative to the amount of the fatty acids.

It has been found that current commercial lipases have varying degrees of effectiveness when used in hydrolyzation reactions, particularly when used in crude and refined fish oil. Improving the selectivity and reaction rate of the lipases would give a higher yield of oil and more efficient processing. For example, some lipases will indiscriminately hydrolyze all available fatty acids from the glyceride. Others will show undesired selectivity towards which fatty acids are hydrolyzed from the glyceride. It would be advantageous to leave the desired LC-PUFAs such as EPA and DHA on the glyceride to more efficiently and effectively enable the concentration of these LC-PUFAs in later downstream processing steps. Identification and isolation of lipases that would allow for such selectivity and/or improved reaction rate would, therefore, be very useful. The inventors have identified isoforms of lipases that are more selective for the desired LC-PUFAs such as EPA and DHA, and have a higher reaction rate.

SUMMARY OF THE INVENTION

Disclosed herein are host cells expressing a polypeptide, wherein the polypeptide hydrolyzes an ester linkage of a triacylglycerol in an oil, methods for using such host cells, and processes for production of a polypeptide that is a lipase using such host cells.

In some embodiments, the polypeptide has at least 90% identity to the amino acid sequence of SEQ ID NO: 1. In some embodiments, the polypeptide has at least 90% identity to the amino acid sequence of SEQ ID NO:2. In some embodiments, the polypeptide has at least 90% identity to the amino acid sequence of SEQ ID NO:3.

In some embodiments, the polypeptide is a lipase. In a preferred embodiment, the polypeptide is an isoform of a lipase. In a more preferred embodiment, the polypeptide is an isoform of a lipase derived from *Candida rugosa* or *Geotrichum candidum*.

In some embodiments, the host cell is a yeast. In a preferred embodiment, the host cell is *Pichia pastoris*.

In some embodiments, the triacylglycerol comprises at least one long-chain polyunsaturated fatty acid (LC-PUFA). In some embodiments, the LC-PUFA comprises docosahexaenoic acid (DHA), eicosapentaenoic acid (EPA), and mixtures thereof. In another embodiment, the LC-PUFA is DHA. In a further embodiment, the LC-PUFA is EPA.

DESCRIPTION OF THE INVENTION

The nucleic acid sequences and deduced amino acid translation sequences listed in the accompanying sequence listing are shown using standard letter abbreviations for nucleotide bases and amino acids, as defined in 37 C.F.R. § 1.822. In the accompanying sequence listing:

SEQ ID NO:1 shows the amino acid sequence of the *Candida rugosa* isoform lipase 1 protein (without alpha-mating factor) from *Pichia Pastoris*:

```
1    APTATLANGD TITGLNAIIN EAFLGIPFAE PPVGNLRFKD PVPYSGSLDG    51
     QKFTSYGPSC MQQNPEGTYE ENLPKAALDL VMQSKVFEAV SPSSEDCLTI   101
     NVVRPPGTKA GANLPVMLWI FGGGFEVGGT STFPPAQMIT KSIAMGKPII   151
     HVSVNYRVSS WGFLAGDEIK AEGSANAGLK DQRLGMQWVA DNIAAFGGDP   201
     TKVTIFGESA GSMSVMCHIL WNDGDNTYKG KPLFRAGIMQ SGAMVPSDAV   251
     DGIYGNEIFD LLASNAGCGS ASDKLACLRG VSSDTLEDAT NNTPGFLAYS   301
     SLRLSYLPRP DGVNITDDMY ALVREGKYAN IPVIIGDQND EGTFFGTSSL   351
     NVTTDAQARE YFKQSFVHAS DAEIDTLMTA YPGDITQGSP FDTGILNALT   401
     PQFKRISAVL GDLGFTLARR YFLNHYTGGT KYSFLSKQLS GLPVLGTFHS   451
     NDIVFQDYLL GSGSLIYNNA FIAFATDLDP NTAGLLVKWP EYTSSSQSGN   501
     NLMMINALGL YTGKDNFRTA GYDALFSNPP SFFV
```

SEQ ID NO:2 shows the amino acid sequence of the *Candida rugosa* isoform lipase 3 protein (without alpha-mating factor) from *Pichia Pastoris*.:

```
1    APTAKLANGD TITGLNAIIN EAFLGIPFAE PPVGNLRFKD PVPYSGSLNG    51
     QKFTSYGPSC MQQNPEGTFE ENLGKTALDL VMQSKVFQAV LPQSEDCLTI   101
     NVVRPPGTKA GANLPVMLWI FGGGFEIGSP TIFPPAQMVT KSVLMGKPII   151
     HVAVNYRVAS WGFLAGDDIK AEGSGNAGLK DQRLGMQWVA DNIAGFGGDP   201
     SKVTIFGESA GSMSVLCHLI WNDGDNTYKG KPLFRAGIMQ SGAMVPSDPV   251
     DGTYGNEIYD LFVSSAGCGS ASDKLACLRS ASSDTLLDAT NNTPGFLAYS   301
     SLRLSYLPRP DGKNITDDMY KLVRDGKYAS VPVIIGDQND EGTIFGLSSL   351
     NVTTNAQARA YFKQSFIHAS DAEIDTLMAA YPQDITQGSP FDTGIFNAIT   401
     PQFKRISAVL GDLAFIHARR YFLNHFQGGT KYSFLSKQLS GLPIMGTFHA   451
     NDIVWQDYLL GSGSVIYNNA FIAFATDLDP NTAGLLVNWP KYTSSSQSGN   501
     NLMMINALGL YTGKDNFRTA GYDALMTNPS SFFV
```

SEQ ID NO:3 shows the amino acid sequence of the *Geotrichum candida* isoform lipase 2 protein (without alpha factor signal peptide or 8×Histamine tag) from *Pichia Pastoris*:

```
1    QAPTAVLNGN EVISGVLEGK VDTFKGIPFA DPPLNDLRFK HPQPFTGSYQ    51
     GLKANDFSPA CMQLDPGNSL TLLDKALGLA KVIPEEFRGP LYDMAKGTVS   101
     MNEDCLYLNV FRPAGTKPDA KLPVMVWIYG GAFVYGSSAA YPGNSYVKES   151
     INMGQPVVFV SINYRTGPFG FLGGDAITAE GNTNAGLHDQ RKGLEWVSDN   201
     IANFGGDPDK VMIFGESAGA MSVAHQLIAY GGDNTYNGKK LFHSAILQSG   251
     GPLPYHDSSS VGPDISYNRF AQYAGCDTSA SANDTLECLR SKSSSVLHDA   301
     QNSYDLKDLF GLLPQFLGFG PRPDGNIIPD AAYELFRSGR YAKVPYISGN   351
     QEDEGTAFAP VALNATTTPH VKKWLQYIFY DASEASIDRV LSLYPQTLSV   401
     GSPFRTGILN ALTPQFKRVA AILSDMLFQS PRRVMLSATK DVNRWTYLST   451
     HLHNLVPFLG TFHGNELIFQ FNVNIGPANS YLRYFISFAN HHDPNVGTNL   501
     LQWDQYTDEG KEMLEIHMTD NVMRTDDYRI EGISNFETDV NLYG
```

DETAILED DESCRIPTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined so as to sub-combinations thereof.

Embodiments identified herein as exemplary are intended to be illustrative and not limiting.

In this specification and in the claims that follow, reference will be made to a number of terms, which shall be defined to have the following meanings:

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

"Optional" or "optionally" means that the subsequently described event or circumstance can or cannot occur, and that the description includes instances where the event or circumstance occurs and instances where it does not.

The term "triacylglycerol" or "TAG" is used to refer to a molecule comprising a glycerol ester of a fatty acid. This term is also used synonymously with "triglyceride" (TG). "Glyceride" is used to refer to mono-, di- and/or triglycerides, as the context dictates.

Polyunsaturated fatty acids (PUFAs) are classified based on the position of the first double bond from the methyl end of the fatty acid; omega-3 (n-3) fatty acids contain a first double bond at the third carbon, while omega-6 (n-6) fatty acids contain a first double bond at the sixth carbon. For example, docosahexaenoic acid (DHA) is an omega-3 long chain polyunsaturated fatty acid (LC-PUFA) with a chain length of 22 carbons and 6 double bonds, often designated as "22:6n-3." A long-chain polyunsaturated fatty acid (LC-PUFA) has a number of carbon atoms from 20 to 24 and the number of unsaturations is 4 or 5. PUFAs and LC-PUFAs can be in free form, ester, or glyceride form.

Sequence Identity and Similarity

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1):387 (1984)), BestFit, BLASTP, BLASTN, and FASTA (Altschul, S. F. et al., J. Mol. Biol. 215:403-410 (1990)). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990)). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Tip or Phe; and, Val to Ile or Leu.

Disclosed herein are host cells expressing a polypeptide, wherein the polypeptide hydrolyzes an ester linkage of a triacylglycerol in an oil comprising at least one long-chain polyunsaturated fatty acid, methods for using such host cells, and processes for production of a polypeptide that is a lipase using such host cells.

In one embodiment, the host cell has the ability of producing triglyceride-hydrolyzing polypeptides in high yield. The ability to produce these polypeptides is conferred to the host cell by transformation of the host cell with a nucleic acid construct comprising a polynucleotide encoding the targeted polypeptide. The transformed host cell's ability to produce these lipases is a combination of the transvection of the lipase-encoded sequence from expression hosts such as *Candida rugosa* or *Geotrichum candidum*, and promoter genes such as AOX or GAP. The lipases are fused to the alpha mating factor of *Saccharomyces cerevisiae* enabling the secretion of recombinant lipases to the culture supernatant. The alpha mating factor is cleaved upon export of the native protein. This also allows the lipase to be harvested without destruction of the host cell.

The amino acid sequence is a lipase that is preferably expressed in excretable form in the transformed host cell and is then excreted in active form out of the host cell. Thus, expression of the amino acid sequence in the host cell produces a lipase which, when transported out of the host cell, has an expression level of greater than 1 U/mL cell culture, preferably at least 2, 3, 4, 5, 10, 20, 40, 60, or 80 U/mL at 28° C. One unit of activity (U) is defined as the amount of enzyme that produced 1 µmol p-nitrophenol per minute under standard conditions (100 mM MOPS buffer pH 7.5, 0.24 mM p-nitrophenyl ester, 37° C.). Determination of the lipase activity, amount of cell culture, and preparation of the cell free lipase were measured by spectrophotometric activity assay as described in the corresponding test method section, with para-nitrophenyl butyrate (p-NPD) as substrate.

A host cell expressing a polypeptide, wherein the polypeptide hydrolyzes an ester linkage of a triacylglycerol in an oil comprising at least one long-chain polyunsaturated fatty acid is preferably a host capable of aerobic fermentation. The host cell further preferably has a high tolerance to ethanol and organic acids like lactic acid, acetic acid or formic acid and sugar degradation products such as furfural and hydroxy-methylfurfural. Any of these characteristics or activities of the host cell may be naturally present in the host cell or may be introduced or modified by genetic modification. A suitable host cell is a microorganism like a bacterium or a fungus, however, most suitable as host cell are yeasts or filamentous fungi. Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form. Yeasts may either grow by budding of a unicellular thallus or may grow by fission of the organism. Preferred yeasts as host cells belong to the genera *Saccharomyces, Kluyveromyces, Candida, Pichia, Schizosaccharomyces, Hansenula, Kloeckera, Schwanniomyces, Geotrichia*, and *Yarrowia*.

In a preferred embodiment, the nucleic acid construct confers to the host cell the ability to generate polypeptides, such as lipase enzymes, and emit them from the cell. The transformed host cell has the ability to grow in various media designed for yeast cultivation. The transformed host cell of the invention thus extracellularly expresses a lipase at a specific activity level dependent on plasmid design and cultivation conditions.

Transformation of host cells with the nucleic acid constructs of the invention and additional genetic modification of host cells, preferably yeasts, as described above, may be carried out by methods well known in the art. Such methods are e.g., known from standard handbooks, such as Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. European Patent Application No. 0 635 574, PCT Publication Nos. WO 98/46772, WO 99/60102 and WO 00/37671.

In some embodiments, the nucleic acid construct comprises a polynucleotide sequence encoding a lipase and used for transformation of a host cell. In the nucleic acid construct, the polynucleotide sequence encoding the lipase preferably is operably linked to a promoter for control and initiation of transcription of the polynucleotide sequence in a host cell. The promoter preferably is capable of causing sufficient expression of the lipase in the host cell to confer to the host cell the ability to generate the lipase and excrete it from the cell. Preferably, the promoter maximizes the lipase production in the host cell. Promoters useful in the nucleic acid constructs of the invention include both constitutive and inducible natural promoters as well as engineered promoters. Promotors having these characteristics are widely available and known to the skilled person. Suitable examples of such promoters include e.g., yeast promoters from glycolytic genes, such as the yeast phosphofructokinase (PPK), triose phosphate isomerase (TPI), glyceraldehyde-3-phosphate dehydrogenase (GPD, TDH3 or GAPDH), pyruvate kinase (PYK), phosphoglycerate kinase (PGK) promoters, TEF1-alpha gene promoters, PHO90, TH11, and AOD promoters; more details about such promoters may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Most preferred are the promoters from the *Pichia* expression vector pD912 (strong methanol inducible AOX promoter) and *Pichia* expression vector pD915 (medium strong constitutive GAP promoter). Other promoters, both constitutive and inducible, and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the lipase is homologous to the host cell in which the lipase isomerase is expressed.

In the nucleic acid construct, the 3'-end of the nucleotide acid sequence encoding the lipase preferably is operably linked to a secretion factor sequence that enables the secretion of recombinant lipases to the culture supernatant and is subsequently cleaved upon export of the lipase. Preferably, the secretion factor sequence is operable in a host cell of choice, such as e.g., the yeast species of choice. In any case the choice of the factor is not critical, it may e.g., be from any yeast gene, although secretion factors may sometimes work if from a non-yeast, eukaryotic, gene. The secretion factor sequence further preferably comprises an alpha mating factor of *Saccharomyces cerevisae*.

Optionally, a selectable marker may be present in the nucleic acid construct. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g., dihydrofolate reductase, hygromycin-B-phosphotransferase, zeocin, 3'-O-phosphotransferase II (kanamycin, neomycin and G418 resistance). Although the use of antibiotic resistance markers may be most convenient for the transformation of polyploid host cells, preferably however, non-antibiotic resistance markers are used, such as auxotrophic markers (URA3, TRP1, LEU2) or the *S. pombe* TPI gene (described by Russell P R, 1985, Gene 40: 125-130). The host cells transformed with the nucleic acid constructs can be marker-gene free. Methods for constructing recombinant marker-gene free microbial host cells are disclosed in European Patent Application No. 0 635 574 and are based on the use of bidirectional markers such as the *A. nidulans* amdS (acetamidase) gene or the yeast URA3 and LYS2 genes. Alternatively, a screenable marker such as Green Fluorescent Protein, lacZ, luciferase, chloramphenicol acetyltransferase, beta-glucuronidase may be incorporated into the nucleic acid constructs of the invention allowing to screen for transformed cells.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g. be based on the yeast 2.mu. or pKD1 (Fleer et al., 1991, Biotechnology 9:968-975) plasmids. Alternatively, the nucleic acid construct may comprise sequences for integration, preferably by homologous recombination. Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987).

In one embodiment, the present invention relates to a host cell expressing a polypeptide, wherein the polypeptide hydrolyzes an ester linkage of a triacylglycerol in an oil comprising at least one long-chain polyunsaturated fatty acid.

In another embodiment, the present invention relates to a method of using a host cell expressing a polypeptide, wherein the polypeptide hydrolyzes an ester linkage of a triacylglycerol in an oil comprising at least one long-chain polyunsaturated fatty acid.

In some embodiments, the host cell expresses a polypeptide having at least 90, 91, 92, 93, 94, 95, 96, 97, 98, 99% identity to the amino acid sequence of SEQ ID NO: 1, wherein the polypeptide hydrolyzes an ester linkage of a triacylglycerol in an oil comprising at least one long-chain polyunsaturated fatty acid. In some embodiments, the host cell expresses a polypeptide having a 90% to 99%, a 91% to 99%, a 92% to 99%, a 93% to 99%, a 94% to 99%, a 95% to 99%, a 96% to 99%, a 97% to 99%, or a 98% to 99% identity to the amino acid sequence of SEQ ID NO:1, wherein the polypeptide hydrolyzes an ester linkage of a triacylglycerol in an oil comprising at least one long-chain polyunsaturated fatty acid.

In another embodiment, the host cell expresses a polypeptide having at least 90, 91, 92, 93, 94, 95, 96, 97, 98, 99% identity to the amino acid sequence of SEQ ID NO: 2, wherein the polypeptide hydrolyzes an ester linkage of a triacylglycerol in an oil comprising at least one long-chain polyunsaturated fatty acid. In some embodiments, the host cell expresses a polypeptide having a 90% to 99%, a 91% to 99%, a 92% to 99%, a 93% to 99%, a 94% to 99%, a 95% to 99%, a 96% to 99%, a 97% to 99%, or a 98% to 99% identity to the amino acid sequence of SEQ ID NO:2, wherein the polypeptide hydrolyzes an ester linkage of a triacylglycerol in an oil comprising at least one long-chain polyunsaturated fatty acid.

In another embodiment, the host cell expresses a polypeptide having at least 90, 91, 92, 93, 94, 95, 96, 97, 98, 99% identity to the amino acid sequence of SEQ ID NO: 3, wherein the polypeptide hydrolyzes an ester linkage of a triacylglycerol in an oil comprising at least one long-chain polyunsaturated fatty acid. In some embodiments, the host cell expresses a polypeptide having a 90% to 99%, a 91% to 99%, a 92% to 99%, a 93% to 99%, a 94% to 99%, a 95% to 99%, a 96% to 99%, a 97% to 99%, or a 98% to 99% identity to the amino acid sequence of SEQ ID NO:3, wherein the polypeptide hydrolyzes an ester linkage of a triacylglycerol in an oil comprising at least one long-chain polyunsaturated fatty acid.

In some embodiments, the polypeptide is a lipase. In a preferred embodiment, the polypeptide is an isoform of a lipase. In a more preferred embodiment, the polypeptide is an isoform derived from *Candida rugosa* or *Geotrichum candidum*.

In some embodiments, the polypeptide that hydrolyzes an ester linkage of a triacylglycerol in an oil is a lipase. In a preferred embodiment, the polypeptide that hydrolyzes an ester linkage of a triacylglycerol in an oil is an isoform of a lipase. In a more preferred embodiment, the polypeptide that hydrolyzes an ester linkage of a triacylglycerol in an oil is an isoform of a lipase derived from *Candida rugosa* or *Geotrichum candidum*.

In some embodiments, the host cell is a yeast. In a preferred embodiment, the host cell is *Pichia pastoris*.

In one embodiment, the lipase is a mixture of isoforms derived from *Candida rugosa*. In a preferred embodiment, the lipase is an isoform derived from *Candida rugosa*. In a more preferred embodiment, the lipase is *Candida rugosa* isoform lipase 1, *Candida rugosa* isoform lipase 3, and mixtures thereof. In one embodiment, *Candida rugosa* isoform lipase 1 has the amino acid sequence of SEQ ID NO:1. In one embodiment, *Candida rugosa* isoform lipase 3 has the amino acid sequence of SEQ ID NO:3.

In one embodiment, the lipase is a mixture of isoforms derived from *Geotrichum candidum*. In a preferred embodiment, the lipase is an isoform derived from *Geotrichum candidum*. In a more preferred embodiment, the lipase is *Geotrichum candidum* isoform lipase 2. In one embodiment, *Geotrichum candidum* isoform lipase 2 has the amino acid sequence of SEQ ID NO:3.

In some embodiments, the triacylglycerol comprises at least one long-chain polyunsaturated fatty acid (LC-PUFA). In some embodiments, the LC-PUFA comprises an omega-3 fatty acid, an omega-6 fatty acid, and mixtures thereof. In a preferred embodiment, the LC-PUFA comprises docosahexaenoic acid (DHA), eicosapentaenoic acid (EPA), docosapentaenoic acid (DPA), arachidonic acid (ARA), gamma-linolenic acid (GLA), dihomo-gamma-linolenic acid (DGLA), stearidonic acid (SDA), and mixtures thereof. In a more preferred embodiment, the LC-PUFA comprises DHA, EPA, and mixtures thereof. In a further embodiment, the LC-PUFA is DHA. In yet a further embodiment, the LC-PUFA is EPA.

In some embodiments, the host cells are yeasts. Preferably the yeast is capable of aerobic fermentation. In one embodiment, the host cell is *Pichia pastoris*. In another embodiment, the host cell is *Escherichia coli*.

In some embodiments, the oil can be derived from marine oils, such as fish oil. Such oils typically contain mixtures of saturated and unsaturated fatty acids, esters, and glycerides thereof, but can be processed to result in a particular mixture of fatty acids (e.g., containing all saturated, all unsaturated, mixtures of both, or mixtures with fatty acids of a certain chain length or range of chain lengths). Any fish oil can be used in the disclosed compounds and methods. Examples of suitable fish oils include, but are not limited to, Atlantic fish oil, Pacific fish oil, Mediterranean fish oil, light pressed fish oil, alkali treated fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, herring oil, mackerel oil, salmon oil, and shark oil, including mixtures and combinations thereof. Non-alkali treated fish oil is also suitable. Other marine oils suitable for use herein include, but are not limited to, squid oil, cuttle fish oil, octopus oil, krill oil, seal oil, whale oil, and the like, including mixtures and combinations thereof. Any marine oil and combination of marine oil can be used in the disclosed compositions and in the disclosed methods to prepare them. Further oils include, a microbial oil that is an algal oil (e.g., oil from a dinoflagellate such as *Crypthecodinium cohnii, Phythium*) or a microbial oil that is a fungal oil (e.g., oil from *Thraustochytrium, Schizochytrium, Mortierella alpina*, or a mixture thereof), and/or plant oil, including mixtures and combinations thereof. In a preferred embodiment, the oil is a crude or unrefined oil.

In one embodiment, the process for the production of a polypeptide that is a lipase comprises the steps of: a) fermenting in a medium a host cell transformed to generate and excrete a polypeptide that is a lipase, as defined herein, whereby the host cell ferments and, concomitantly generates and excretes the polypeptide that is a lipase; and optionally, b) recovery of the polypeptide that is a lipase. The fermentation process is preferably run at a temperature that is optimal for the transformed host cell. Thus, for most yeasts or fungal host cells, the fermentation process is performed at a temperature which is less than 38° C. For yeast or filamentous fungal host cells, the fermentation process is preferably performed at a temperature which is lower than 35, 33, 30 or 28° C. and at a temperature which is higher than 20, 22, or 25° C. The fermentation medium may be further optimized to enhance these process steps by any variety of medium compositions known to those skilled in the art. In a preferred embodiment, the polypeptide that is a lipase is selected from the group consisting of *Candida rugosa* lipase 1, *Candida rugosa* lipase 3, and *Geotrichum candida* lipase 2.

EXAMPLES

Test Methods

Spectrophotometric activity assay: To determine the activity of the lipases, a spectrophotometric assay at 37° C. was used in which p-nitrophenylesters are hydrolyzed. The increase of absorbance at 410 nm caused by the formed p-nitrophenol could be measured and correlates with the enzyme activity. One unit of activity (U) was defined as the amount of enzyme that produced 1 µmol p-nitrophenol per minute under the used conditions. Therefore, a reaction mixture containing 100 mM MOPS buffer pH 7.5, 0.24 mM p-nitrophenylester and 38 µl/ml CFE in a suitable dilution was used as well as blanks containing buffer instead of CFE and the absorbance change was recorded for 5 min. Based on this Δabs/min the volumetric activity (U/ml, see equation 1) and the protein specific activity (U/mg total protein, see equation 2) could be calculated. Measured were the CFE containing the soluble protein fraction (Soluble) and the CFE containing the total protein (Total). In first instance, p-nitrophenylbutyrat (pNPB) was used as substrate.

$$\frac{U}{ml} = \left(\left(\frac{\Delta abs_{CFE}}{min} - \frac{\Delta abs_{blank}}{min}\right) * Df * 26\right) / (\varepsilon * d) \quad (1)$$

with: $Df$ = dilution factor of the CFE $\varepsilon = 12.643 \; (\mu mol/ml)^{-1} * cm^{-1}$ $d$ = path length cuvette $$\frac{U}{mg} = \text{volumetric activity } \frac{U}{ml} / \text{protein concentration } \frac{mg}{ml} \quad (2)$$

Determination of free fatty acids: To determine the percentage of free fatty acids (% FFA) an endpoint titration with Titrino 718 was used. 50 ml of a solvent (toluene/isopropanol/water=500/500/10) was mixed with two drops of phenolphthalein (0.8% (w/w) in isopropanol) and titrated with 0.15 M KOH (10.0 g KOH dissolved in 50 ml water and filled up with 950 ml Ethanol) till color of the solutions stayed pink for 10-15 seconds. To determine the titer, a known amount of benzoic acid was added to the solution and titrated. The titer was calculated as described in equation 3 and for further calculation, the mean of three independent titer-determinations was used. For measuring samples, a known amount of the oil layer of the sample was added to the pink solvent, mixed well and the titrated back to pink. The percentage of FFA was calculated as described in equation 4.

$$\text{titer} = m/Mw(Ba)/V(KOH) \quad (3)$$

with: titer in mol/l
m=mass of used benzoic acid in g
Mw(Ba)=molecular weight of benzoic acid (122.12 g/mol)
V(KOH)=volume of used 0.15 M KOH in l $$\% \; FFA = V(KOH)*\text{titer}*Mw(KOH)/m \quad (4)$$

with: titer in mol/l
m=mass of used sample in g
Mw(KOH)=molecular weight of KOH (56.1 g/mol)
V(KOH)=volume of used 0.15 M KOH in l Determination of EPA and DHA concentration in oil phase (on glycerol) by LC-MS: For the analysis of EPA and DHA concentration, approximately 40 mg of the oil layer were dissolved in 25 ml tetrahydrofuran and further diluted 1:4. The samples were analyzed by LC-MS per typical protocols for such instruments. Column used was a Waters Acquity UPLC BEH C18 50×2.1 mm ID 1.8 μm with pre-column VanGuard. The system was calibrated for DHA and EPA. Calibration curves were generated for both compounds. The results showed that EPA and DHA were well separated thus allowing for accurate calculations of free fatty acids for each.

Example 1—Expression of Candida rugosa Lipase Isoforms in Pichia pastoris

The isoforms in two commercially available Candida rugosa lipases, Amano AY and BioCataysts Lipomod 034, were measured by protein-MS sequencing. 5 CR isoforms were found and the two major isoforms identified in both lipases were CR Lip1 and CR Lip3. Genes for all 5 isoforms were prepared and codon-optimized for expression in Pichia pastoris by DNA2.0 (Menlo Park, Calif.). Lipase genes were fused to the alpha mating factor gene of Saccharomyces cerevisiae enabling the secretion of recombinant lipases to the culture supernatant. The alpha mating factor was cleaved upon export of the native protein. Two expression vectors were prepared, one having an AOX promoter (pD912) and the other having a GAP promoter (pD915), and each individually cloned into Pichia pastoris. In pD912, the gene of interest is cloned downstream and in fusion with the alpha-factor and is under control of the strong methanol inducible AOX promoter. In pD915, the gene of interest is cloned downstream and in fusion with the alphafactor and is under control of the medium strong constitutive GAP promoter. For both pD912 and pD915, zeocin was the selection marker and upon integration into the Pichia genome, pUC origin necessary for propagation in E. coli was removed. 10 of the DNA constructs were prepared by DNA2.0 (Menlo Park, Calif.) and used in each of 2 vectors prepared by DNA2.0. A positive control was also used (pJ912_cutinase from DNA2.0).

Transformation of E. coli with the Pichia Expression Vectors pD912 and pD915 Containing Candida rugosa Lipase Isoform Genes For transformation of P. pastoris, a high amount of plasmid DNA is needed. The plasmid DNA prepared by DNA2.0 was propagated in E. coli. Competent cells were generated. The resulting stock was converted to a glycerol stock and the remaining culture was used to extract plasmid DNA.

Extraction of Plasmid-DNA from E. coli

Extraction of plasmid-DNA from the remaining culture was achieved by using the standard protocol from Qiagen ("plasmid DNA purification using Qiagen Plasmid Midi Kit"). The obtained plasmid DNA was analyzed on 0.8% agarose gel and DNA concentration was measured. The results are shown in Table 1.

TABLE 1

DNA Concentration in Midiprep Samples

| Sample ID | DNA concentration (ng/μl) |
|---|---|
| 912-1 | 685.9 |
| 912-2 | 553.2 |
| 912-3 | 749.6 |
| 912-4 | 683.5 |
| 912-5 | 825.5 |
| 915-1 | 700.5 |
| 915-2 | 409.9 |
| 915-3 | 613.5 |
| 915-4 | 670.2 |
| 915-5 | 793.5 |
| cutinase | 578.2 |

Transformation of Pichia pastoris PPS9010 with pD912 and pD915 Containing Candida Rugosa Lipase Isoform Genes Plasmid linearization: The plasmids, which were propagated and therefore available in higher amount, had to be linearized (linear DNA is necessary for transformation of Pichia pastoris). For linearization the following restrictions enzymes were used: For pD912-constructs SacI was used (incubation-temperature 37° C.) and for pD915-constructs SwaI was used (incubation-temperature 25° C.).

To 20 μg DNA (obtained from the Midiprep), 10 μl 10× buffer and 2.5 μl of the restriction-enzyme was added. The mixture was filled up to 100 μl with water. The incubation was run at the appropriate temperature for the restriction enzyme for two hours. The enzymes were then deactivated by exposing the mixture to 65° C. for 20 min. 1 μl mixture was analyzed on 0.8% agarose-gel to verify that the restriction was successful. The achieved linearized DNA was purified using Quiagen PCR Purification Kit by following the supplier's manual. After purification, DNA concentration was measured. The results are shown in Table 2.

TABLE 2

DNA Concentration in purified, linearized plasmid DNA

| Sample ID | DNA concentration (ng/μl) |
|---|---|
| 912-1 | 685.9 |
| 912-2 | 553.2 |
| 912-3 | 749.6 |
| 912-4 | 683.5 |
| 912-5 | 825.5 |
| 915-1 | 700.5 |
| 915-2 | 409.9 |
| 915-3 | 613.5 |
| 915-4 | 670.2 |
| 915-5 | 793.5 |
| cutinase | 578.2 |

Preparation of Competent Pichia pastoris Cells 5 ml YPD medium was inoculated with Pichia pastoris PPS9010 cells from the glycerol stock using an inoculation loop and was incubated overnight at 30° C. and 180 rpm. This culture was used to inoculate 100 ml fresh YPD medium to an $OD_{600}$ of 0.15-0.2 and this was then incubated at 30° C. and 120 rpm. When $OD_{600}$ reached 1.3-1.5, the culture was filled into two 50 ml Falcon tubes and centrifuged at 500*g for 10 min at 4° C. The supernatant was decanted and discarded. The pellets were re-suspended in 50 ml ice cold sterilized, ultrapure water and centrifuged at 500 *g for 5 min at 4° C. This supernatant was also decanted and discarded. The pellets were re-suspended again in 50 ml ice cold sterilized, ultrapure water and centrifuged at 500 *g for 5 min at 4° C. This supernatant was also decanted and discarded. The cells were then re-suspended in 20 ml ice cold, sterilized 1M sorbitol and centrifuged at 500 *g for 5 min at 4° C. The supernatant was again decanted and discarded. The cells were then finally re-suspended in 250 μl 1M sorbitol.

Transformation of Competent *Pichia pastoris*

The prepared competent *Pichia* cells were transformed with the linearized plasmids, which were magnified in quantity by using *E. coli* as described above. To 100 µl competent *Pichia* cells, 10 µl linearized plasmid (2-4 µg) was added and the suspension was transferred to an electroporation cuvette with a gap of 2 mm. The cells were incubated on ice for 5 min and then electroporated at 1500V, 200 Ω, 25 µF. To this mixture was added 1 ml ice cold 1M sorbitol and the mixture was incubated at 30° C. for 1 hour. The mixture was then centrifuged at 1000 *g for 5 min at 21° C. and the supernatant decanted. The pellet was re-suspended in the remaining droplet of supernatant. Each colony was transferred to 5 ml YPD medium with 200 µg/ml zeocin with inoculation loop and incubated overnight at 28° C. and 180 rpm. For long term storage 1 ml of the culture was mixed with 0.5 ml 50% glycerol, shaken for 15 min at room temperature, and stored at −80° C.

Verification of Clone Expression and Activity

Tributyrin agar plate assay and SDS-PAGE analysis were run on all samples to verify that all tested clones showed activity towards tributyrin and that the expected lipase bands were observed. Activity of the cultures was measured by spectrophotometric activity assay, with p-NPD as the substrate. Protein content of the samples was analyzed by Bradford reagent following standard procedures. The results showed CR Lip1 clones had high level expression of the lipase. No activity was detected for any of the CR Lip5 clones, while moderate activity was measured for several CR Lip3 and CR Lip4 clones. Activities of CR Lip2 clones was typically very low. Shake flask expression needed to be performed to receive more constant growth conditions and therefore more reliable data.

Shake Flask Expression of AOX and GAP Constructs

For shake-flask expression of AOX-constructs, 25 ml BMGY medium in a 300 ml flask with baffles was inoculated using the glycerol stock. This preculture was incubated at 28° C. at 110 rpm for 24 hours. The cells were harvested by centrifugation (3000 *g, 5 min, room temperature), re-suspended in 50 ml BMMY medium and filled into a 1000 ml flask with baffles and foam plug. For expression, the culture was incubated at 28° C. and 110 rpm for 96 hours. To maintain induction 250 µl methanol were added once a day. After 96 hours, the culture was centrifuged (3000 *g, 5 min, 4° C.) and the supernatant transferred to a separate tube, which was stored at −20° C.

For shake-flask expression of GAP-constructs, 25 ml YPD medium in a 300 ml flask with baffles was inoculated using the glycerol stock. This preculture was incubated at 28° C. at 110 rpm overnight. The cells were harvested by centrifugation (3000 *g, 5 min, room temperature), re-suspended in 100 ml YPD medium and filled into a 1000 ml flask with baffles and foam plug. For expression, the culture was incubated at 28° C. and 110 rpm for 96 hours. After 96 hours, the culture was centrifuged (5000 *g, 10 min, 4° C.) and the supernatant transferred to a separate tube, which was stored at −20° C.

Spectrophotometric Activity Assay

Activity of the culture supernatants was measured by the spectrophotometric activity assay described above. As substrate, p-NPD (p-nitrophenyl decanoate) was used.

Protein content of the samples was analyzed by Bradford reagent following standard procedures. The specific activity of the samples in U/mg total protein was compared to the activities of 4 other commercial lipases from *Alcaligness sp.* (Al-1, Al-2, Al-3 and Al-4) and the commercial CRL preparation L11. The results are shown in Table 3.

TABLE 3

Activity numbers and protein content of *Pichia pastoris* shake flask expressions.

| System | Clone | Vol. activity (U/ml cell culture] p-NPD | Total protein content (mg/ml culture supernatant) | Specific activity (U/mg total protein in culture supernatant) p-NPD |
|---|---|---|---|---|
| AOX | 1.1 | 132.8 | 0.097 | 1362.4 |
| | 1.4 | 0.5 | 0.085 | 5.9 |
| | 2.2 | 0.1 | 0.087 | 1.3 |
| | 3.3 | 5.9 | 0.081 | 72.2 |
| | 3.4 | 5.2 | 0.079 | 65.9 |
| | 4.1 | 16.5 | 0.094 | 175.5 |
| | 4.2 | 18.5 | 0.097 | 190.2 |
| GAP | 1.3 | 80.9 | 0.071 | 1136.2 |
| | 1.5 | 97.6 | 0.091 | 1070.1 |
| | 2.2 | 0.5 | 0.092 | 5.4 |
| | 3.2 | 5.9 | 0.107 | 54.5 |
| | 4.4 | 9.4 | 0.121 | 77.4 |
| | 4.5 | 10.6 | 0.098 | 107.9 |
| | 5.1 | 0.0 | 0.127 | 0.0 |
| other | Al-1 | | | 717.0 |
| | Al-2 | | | 83.8 |
| | Al-3 | | | 142.5 |
| | Al-4 | | | 63.0 |

Example 2—Comparison of Expression Levels in *P. pastoris* and *E. coli*

For comparison, expression of lipase isoforms in *Escherichia coli* was also performed. The genetic constructs were ordered as synthetic DNA from DNA2.0 and cloned in expression vectors harboring the neomycin resistance gene; the gene of interest is induced by L-arabinose via the pBAD promoter. The results are shown in Table 4.

TABLE 4

Comparison of achieved expression levels of *P. pastoris* and *E. coli*

| Isoform | Organism | System | Expression conditions | U/ml cell culture |
|---|---|---|---|---|
| CR Lip3 | *P. pastoris* | AOX | shake flask, 4 days | 5.8 (p-NPD) |
| CR Lip3 | *P. pastoris* | GAP | shake flask, 4 days | 5.9 (p-NPD) |
| CR Lip3 | *E. coli* | BAD | shake flask, 1 day | ~0.8 (p-NPD) |
| CR Lip4 | *E. coli* | BAD | shake flask, 1 day | ~15 (p-NPD) |
| CR Lip4 | *P. pastoris* | AOX | shake flask, 4 days | ~18 (p-NPD) |
| CR Lip4 | *P. pastoris* | GAP | shake flask, 4 days | ~10.6 (p-NPD) |
| CR Lip1 | *P. pastoris* | AOX | shake flask, 4 days | 130 (p-NPD) |
| CR Lip1 | *P. pastoris* | GAP | shake flask, 4 days | 97.6 (p-NPD) |
| CR Lip1 | *E. coli* | BAD | shake flask, 1 day | ~0.09 (p-NPD) |
| CR Lip2 | *P. pastoris* | AOX | shake flask, 4 days | 0.1 (p-NPD) |
| CR Lip2 | *P. pastoris* | GAP | shake flask, 4 days | 0.5 (p-NPD) |
| CR Lip2 | *E. coli* | BAD | shake flask, 1 day | ~0.05 (p-NPD) |

Example 3—*Candida rugosa* Lipase Hydrolyzation Experiments

To test the *Candida rugosa* lipase isoforms prepared according to Example 1 on the hydrolysis of fish oil, reactions at 35° C. were set up in pH-stat equipment in 40 ml scale without titration. The commercially available *Candida rugosa* lipase AY-30 from Amano (referred to as CRL11) was used as a comparative lipase. Due to the poor activity of CR Lip 2 and CR Lip5, only CR Lip1, CR Lip3 and CR Lip4 were used. The fish oil concentration was 50% (v/v). For CR Lip1 and CR Lip4, 8.6 U (based on p-NPD activity) per g fish oil were used corresponding to 0.1%

(w/w) E/S for the commercial lipase. As buffer, 50 mM KPi pH 7.5 was used. Because of the low enzyme amount the enzyme concentration for CR Lip3 was limited to 6.8 U per g fish oil and for CR Lip2 to 0.9 U (corresponding to 0.01% (w/w) E/S for the commercial lipase).

When possible, the fish oil was stirred at 2000 rpm with the buffer for approximately half an hour in the pH-stat before adding the enzyme while the pH was monitored. After starting the reaction by adding the enzyme, 2 ml samples were taken at different points in time, at 0 hours, 1 hour, 4 hours, 18 hours and 24 hours. These samples were analyzed with regard to the concentration of free fatty acids (FFA) and the EPA and DHA concentrations. To get all the free fatty acids into the oil layer, the emulsion was acidified with 3 M HCl, mixed well and centrifuged to separate the layers. If necessary, the samples were liquefied by heating up in an oven at 60° C. for some minutes.

Results of the hydrolyzation are shown in Tables 5 and 6 and illustrate the conversion and selectivities of the reactions. For the sake of comparison, extents of conversion are used to compare the selectivity of the commercial comparative example CRL11 sample to the CR Lip1, CR Lip3 and CR Lip4 samples since it is expected that, as the reaction runs to 100% conversion, all selectivity will be lost by all enzymes. It is useful, therefore, to use the extent of conversion as the milestone for comparison rather than time of reaction. It is expected that the time of reaction will vary for different enzymes isoforms and since time of reaction can be optimized by many different conditions it is recorded to make sure that reasonably times of reactions are observed, however, it is not used as a milestone for comparison.

TABLE 5

Effect of *Candida rugosa* lipase on EPA in FFA

| Sample | Oil (mg/mL)[1] | % Total FFA loss | EPA in oil (mg/mL) | % EPA loss[2] | % EPA loss in FFA[3] |
|---|---|---|---|---|---|
| CRL11 | 0.344 | −0.3 | 0.00004 | −0.01 | −3.63 |
|  | 0.356 | −11.2 | 0.00149 | −0.42 | −3.74 |
|  | 0.337 | −18.6 | 0.00284 | −0.84 | −4.54 |
|  | 0.348 | −29.5 | 0.00492 | −1.41 | −4.79 |
|  | 0.278 | −31.6 | 0.00447 | −1.61 | −5.09 |
| CR Lip1 | 0.329 | −0.2 | 0.00002 | −0.01 | −2.93 |
|  | 0.385 | −6.1 | 0.00070 | −0.18 | −2.97 |
|  | 0.361 | −11.4 | 0.00113 | −0.31 | −2.74 |
|  | 0.342 | −20.1 | 0.00288 | −0.84 | −4.19 |
|  | 0.37 | −21.8 | 0.00363 | −0.98 | −4.51 |
| CR Lip3 | 0.356 | −0.2 | 0.00005 | −0.01 | −3.4 |
|  | 0.296 | −6.8 | 0.000 | −0.04 | −0.86 |
|  | 0.371 | −12.1 | 0.00031 | −0.09 | −0.91 |
|  | 0.411 | −22.7 | 0.00111 | −0.27 | −1.39 |
|  | 0.5 | −24.7 | 0.00103 | −0.34 | −1.69 |
| CR Lip4 | 0.394 | −0.4 | 0.00002 | −0.01 | −2.88 |
|  | 0.454 | −5.1 | 0.00136 | −0.46 | −6.76 |
|  | 0.34 | −10.0 | 0.00275 | −0.74 | −6.15 |
|  | 0.411 | −19.4 | 0.00811 | −1.97 | −8.71 |
|  | 0.305 | −20.0 | 0.01053 | −2.11 | −8.53 |

[1]Oil = concentration of EPA and DHA measured after diluting with THF
[2]% EPA loss is % of free fatty acid EPA = (EPA in oil/oil) × 100
[3]% EPA loss in FFA is % of free EPA related to the total loss of FFA = (% EPA loss/% Total FFA loss) × 100

TABLE 6

Effect of *Candida rugosa* lipase on DHA in FFA

| Sample | Oil (mg/mL)[1] | % Total FFA loss | DHA in oil (mg/mL) | % DHA loss[2] | % DHA loss in FFA[3] |
|---|---|---|---|---|---|
| CRL11 | 0.344 | −0.3 | 0.00003 | −0.1 | −2.87 |
|  | 0.356 | −11.2 | 0.00011 | −0.03 | −0.26 |
|  | 0.337 | −18.6 | 0.00018 | −0.05 | −0.28 |
|  | 0.34 | −29.5 | 0.00034 | −0.10 | −0.33 |
|  | 0.278 | −31.6 | 0.00030 | −0.11 | −0.34 |
| CR Lip1 | 0.326 | −0.2 | 0.00002 | −0.01 | −2.77 |
|  | 0.385 | −6.1 | 0.00003 | −0.01 | −0.13 |
|  | 0.361 | −11.4 | 0.00004 | −0.01 | −0.09 |
|  | 0.342 | −20.1 | 0.00009 | −0.03 | −0.13 |
|  | 0.37 | −21.8 | 0.00009 | −0.03 | −0.12 |
| CR Lip3 | 0.394 | −0.4 | 0.00002 | −0.01 | −1.50 |
|  | 0.454 | −5.1 | 0.00004 | −0.01 | −0.15 |
|  | 0.34 | −10.0 | 0.00003 | −0.01 | −0.10 |
|  | 0.411 | −19.4 | 0.00011 | −0.03 | −0.13 |
|  | 0.305 | −20.0 | 0.00008 | −0.03 | −0.13 |
| CR Lip4 | 0.356 | −0.2 | 0.00002 | −0.01 | −2.87 |
|  | 0.296 | −6.8 | 0.00003 | −0.01 | −0.13 |
|  | 0.371 | −12.1 | 0.00004 | −0.01 | −0.09 |
|  | 0.411 | −22.7 | 0.00014 | −0.03 | −0.15 |
|  | 0.5 | −24.7 | 0.00016 | −0.03 | −0.13 |

[1]Oil = concentration of EPA and DHA measured after diluting with THF
[2]% DHA loss is % of free fatty acid DHA = (DHA in oil/oil) × 100
[3]% DHA loss in FFA is % of free DHA related to the total loss of FFA = (% DHA loss/% Total FFA loss) × 100

Example 4—*Geotrichum candidum* Lipase Hydrolyzation Experiments

In these examples, the lipase-encoding polynucleotide sequences from *Geotrichum candidum* were identified and expressed in *Pichia pastoris* as described in Example 1 above. The commercially available *Candida rugosa* lipase AY-30 from Amano (referred to as CRL11) was used as a comparative lipase.

For each sample (GC Lip1, GC Lip 2 and CRL11), the following process was used: About 20 g fish oil, 3 mL of a 0.95 mg/mL lipase solution, and 12.0 mL of BES buffer (50 mM, pH 7.0) were placed in a 100 mL flask, and stirred at 37° C. at 360 rpm under $N_2$ gas. The reaction progress was monitored by monitoring the acid value by the method described above, Determination of free fatty acids. The reaction was stopped by heating to 85° C. for 10 minutes. The mixture was washed with 25 mL of brine and 25 mL of water, and the oil dried under vacuum (1 torr). The glycerides and fatty acids were separated as follows: 10 g of oil was added to 75 mL of hexane and 25 mL of ethyl acetate. The organic layer was then extracted twice with a solution 40 mL of 0.5M sodium hydroxide and 40 mL of ethanol. The upper organic layer was then washed with water; solvent was removed under reduced pressure and dried under high vacuum to give the glycerides. The lower alkaline layer was then acidified to pH 1 with 3M HCl, and extracted with 75 mL of hexane and 75 mL of chloroform, and the combined organics evaporated to give the fatty acid layers. The fatty acid profiles of the separated glyceride and fatty acids were determined by the EP2.4.29 method. Results are shown in Tables 7 and 8.

The experiment was repeated using GC Lip2 and an oil composition which contains about 22% EPA and 10% DHA. The results are shown in Tables 9 and 10.

TABLE 7

Effect of *Geotrichum candidum* lipase on EPA in FFA on 18:15 oil

| Sample | % FFA | EPA FFA in oil (mg/g) | % EPA loss in FFA |
|---|---|---|---|
| Starting oil | 0.1 | 0 | n/a |
| CRL11 | 26 | 48 | 5.4 |
| GC Lip1 | 14 | 53 | 5.6 |
| GC Lip1 | 14 | 54 | 6.1 |
| GC Lip2 | 27 | 28 | 3.0 |
| GC Lip2 | 25 | 31 | 3.3 |

TABLE 8

Effect of *Geotrichum candidum* lipase on DHA in FFA on 18:15 oil

| Sample | % FFA | DHA FFA in oil (mg/g) | % DHA loss in FFA |
|---|---|---|---|
| Starting oil | 0.1 | 0 | n/a |
| CRL11 | 26 | 15 | 1.6 |
| GC Lip1 | 14 | 8 | 0.9 |
| GC Lip1 | 14 | 11 | 1.1 |
| GC Lip2 | 27 | 11 | 1.2 |
| GC Lip2 | 25 | 14 | 1.6 |

TABLE 9

Effect of *Geotrichum candidum* lipase on EPA in FFA on 22:10 oil

| Sample | % FFA | EPA FFA in oil (mg/g) | % EPA loss in FFA |
|---|---|---|---|
| Starting oil | 0.1 | 0 | n/a |
| CRL11 | 24.1 | 56 | 5.8 |
| GC Lip2 | 17.3 | 24 | 2.8 |
| GC Lip2 | 21.7 | 28 | 2.9 |

TABLE 10

Effect of *Geotrichum candidum* lipase on DHA in FFA on 22:10 oil

| Sample | % FFA | DHA FFA in oil (mg/g) | % DHA loss in FFA |
|---|---|---|---|
| Starting oil | 0.1 | 0 | n/a |
| CRL11 | 24.1 | 10 | 1.0 |
| GC Lip2 | 17.3 | 8 | 0.9 |
| GC Lip2 | 21.7 | 8 | 0.9 |

---

What is claimed is:

1. A method of obtaining at least one long-chain polyunsaturated fatty acid (LC-PUFA) from a triacylglycerol in an oil that comprises the at least one LC-PUFA, wherein said LC-PUFA comprises eicosapentaenoic acid (EPA), docosahexaneoic acid (DHA), or combinations thereof; the method comprising: hydrolyzing at least one ester linkage in said triacylglycerol with a lipase, wherein said lipase has at least 90% sequence identity to the amino acid sequence of SEQ ID NO:1, SEQ ID NO:2, or SEQ ID NO:3.

2. The method of claim 1, wherein the lipase is obtained by expressing it in a Pichia pastoris host cell.

3. The method of claim 1 or claim 2, wherein the lipase has a 90% to 99% sequence identity to the amino acid sequence of SEQ ID NO:1, SEQ ID NO:2, or SEQ ID NO:3.

4. The method of claim 1, wherein the lipase has the amino acid sequence of SEQ ID NO: 1.

5. The method of claim 1, wherein the lipase has the amino acid sequence of SEQ ID NO:2.

6. The method of claim 1, wherein the lipase has the amino acid sequence of SEQ ID NO:3.

7. The method of claim 1, wherein the oil is a crude or unrefined oil.

8. The method of claim 1, wherein the oil is a marine oil.

9. The method according to claim 2, wherein said *Pichia pastoris* host cell is transformed with a nucleic acid construct comprising a polynucleotide encoding the lipase.

* * * * *